United States Patent [19]

Barach et al.

[11] Patent Number: 4,720,460

[45] Date of Patent: Jan. 19, 1988

[54] PROCESS FOR PRESERVING ACID PRODUCING BACTERIA AND COMPOSITIONS PRODUCED THEREBY

[75] Inventors: Jeffrey T. Barach, Elkhart; Bassie J. Kamara, Mishawaka, both of Ind.

[73] Assignee: Miles Laboratories, Inc., Elkhart, Ind.

[21] Appl. No.: 719,895

[22] Filed: Apr. 4, 1985

[51] Int. Cl.$^4$ .................. C12N 1/04; C12N 1/20; A01N 63/00; A23C 9/12

[52] U.S. Cl. ............................ 435/260; 435/253; 424/93; 426/43

[58] Field of Search .............. 435/253, 260; 424/93; 426/34, 42, 43

[56] References Cited

U.S. PATENT DOCUMENTS

| | | | |
|---|---|---|---|
| 1,918,053 | 7/1933 | Barach et al. | 435/260 |
| 3,677,897 | 7/1972 | Jeffreys | 435/260 X |
| 3,897,307 | 7/1975 | Porubean et al. | 426/61 |
| 4,205,132 | 5/1980 | Sandine et al. | 435/260 |
| 4,217,419 | 8/1980 | Suzuki | 435/253 |
| 4,308,287 | 12/1981 | Kahn et al. | 426/43 |
| 4,345,032 | 8/1982 | Hata | 435/260 X |
| 4,482,255 | 8/1984 | Sandine et al. | 426/34 X |
| 4,518,696 | 5/1985 | Gehrman et al. | 435/260 X |

OTHER PUBLICATIONS

Thunell, Sandine and Bodyfelt, "Frozen Starters from Internal-pH-Control-Grown Cultures", *J. Dairy Sci.*, 67:24–36 (1984).

Morichi, "Preservation of Lactic Acid Bacteria by Freeze-Drying" *Japan Agricultural Research Qtrly*, vol. 8, No. 3, 171–176 (1974).

Lim and Moss, "Microencapsulation of Living Cells & Tissues", *Journal of Pharmaceutical Sciences*, vol. 70, No. 4, 351–354 (1981).

Smith, Benedict and Palumbo, "Protection Against Heat-Injury in Staphylococcus aureus by Solutes", *J. of Food Protection*, vol. 45, No. 1, 54–58 (1972).

Cowell, Koburger and Weese, "Storage of Lactic Streptocci. I. Effect of pH on Survival and Endogenous Metabolism in Phosphate Buffer", W. Virginia University Agricultural Experiment Station, Paper No. 859, 356–369 (1966).

*Primary Examiner*—Esther M. Kepplinger
*Assistant Examiner*—Shawn P. Foley
*Attorney, Agent, or Firm*—Jerome L. Jeffers

[57] ABSTRACT

Described is a method to stabilize or preserve acid-producing bacteria in a buffered solution. A carrier may be added that is not a specific substrate for the bacteria in order to give texture, most preferably the carrier being polyethylene glycol or sodium alginate. Optionally, other ingredients such as anti-oxidants, mold inhibitors, and/or salts may be added. These compositions may be stored at temperatures above freezing for a time from a few days up to about 2 months or longer.

9 Claims, No Drawings

PROCESS FOR PRESERVING ACID PRODUCING BACTERIA AND COMPOSITIONS PRODUCED THEREBY

This invention relates to the field of preserving or stabilizing acid-producing bacteria. More particularly, the invention relates to a method of preserving bacteria that not only obviates freezing but also facilitates storage for long periods of time at temperatures higher than freezing.

BACKGROUND OF THE INVENTION

Acid-producing bacteria are used extensively in the manufacture of fermented meat products and silage, as well as in the manufacture of yogurt, cheese, and the like. Lactic acid-producing bacteria are particularly useful in these manufacturing processes. Typical methods for storing these bacteria involve freezing, freeze-drying, and/or microencapsulation.

Freezing has been widely used for storage of microorganisms, and extensive research has been conducted to determine the optimum conditions for maintenance of maximum activity in frozen cultures. See, for instance, "Frozen Starters from Internal pH-Control-Grown Cultures", Technical Paper No. 6427, Oregon Agricultural Experiment Station, Journal of Dairy Science, Vol. 67, No. 1, (1984), Thunnel and Sandine.

Additionally, for over 20 years, freeze-drying (lyophilization) has been employed in order to preserve lactic acid-producing bacteria. See, for instance, Morichi, T., "Preservation of Lactic Acid Bacteria by Freeze-drying", JARQ, No. 3, Pages 170–176 (1974). Also, Suzuki in U.S. Pat. No. 4,217,419 (1980), discloses lyophilization of a suspension of Lactobacillus containing glucose and sodium alginate.

However, there are many problems accompanying these processes. As the freezing takes place, it kills some of the cells. Likewise, when it is decided to rehydrate the stored material, the rehydration process kills additional cells. Thus, carriers are employed to protect the culture during the freezing and/or freeze-drying process. Typical carriers are fermentable carbohydrates, such as glucose, lactose or sucrose. The presence of the fermentable carbohydrates, however, will cause the microorganism to produce acid, resulting in injury and/or death to some of the bacterial cells due to the reduction in pH to a level below that which is optimal.

Encapsulating techniques and encapsulated products for the controlled release of product as a function of the destruction of the encapsulating material over a period of time are also well established in the prior art as methods to preserve microorganisms. By protecting microorganisms from the outside environment, the capsule enables the microorganisms to continue to function. For instance, Lim and Moss, "Microencapsulation of Living Cells and Tissues", Journal of Pharmaceutical Sciences, Vol. 70, No. 4, Pages 351–354 (April, 1981), disclose a microencapsulation procedure for viable cells using calcium chloride to gel cells suspended in sodium alginate droplets.

More recent studies relate to enhancing preservation of microorganisms without using the well established freezing, freeze-drying, or microencapsulation techniques.

For instance, use of a salt to preserve microorganisms without freezing is shown in U.S. Pat. No. 4,308,287 (Kahn and Eapen). This patent discloses a method to enhance preservation of yogurt (which contains acid producing bacteria) by using quinine salts.

Another item of literature disclosing the use of a salt for preservation is Smith, Benedict, and Palumbo, "Protection Against Heat Injury in *Staphylococcus aureus* by Solute", Journal of Food Protection, Vol. 45, No. 1, Pages 54–58, (January, 1982). This article discloses the use of salts such as sodium citrate, KCl, $NaNO_3$, $Na_2SO_4$, $Na_2HPO_4$, $NH_4Cl$, $CaCl_2$, and LiCl for protection against heat-injury with a concomitant decrease in the number of injured *S. aureus* cells over a 90-minute heating-time interval at 49° C.

Storage at 4° C. of suspensions of *Streptococcus lactis* E and *S. cremoris* using lactose as the carrier is disclosed in Cowell, Koburger, and Weese, "Storage of Lactic Streptococci. I. Effect of pH on Survival and Endogeneous Metabolism in Phosphate Buffer", West Virginia University Agricultural Experiment Station, Paper No. 859 Pages 365–369, (January, 1966). However, as can be seen from FIG. 2 on Page 366 of this reference, a decrease in activity or viability starts around 5 days and becomes substantial by 10 days, even when the lactose-containing suspension is buffered at the optimum pH of 8.5. Thus, Cowell et al do not show how to maintain constant viability for storage of acid-producing bacteria at a temperature above freezing. Rather, they show that buffering at a pH of 8.5 achieves a reduction in loss of viability for storage of lactose-containing suspensions of bacteria at 4° C.

SUMMARY OF THE INVENTION

Therefore, the present invention provides for a method to preserve acid-producing bacteria comprising admixing the bacteria in a stabilizing amount of an aqueous buffered solution free of a carrier that is a specific substrate for the bacteria.

ADVANTAGES OF THE INVENTION

It is an object of the present invention to provide a method for the stabilization or preservation of acid-producing bacteria. The preservation may be at temperatures below freezing. However, the object of the present invention is that the method contemplates storage of the bacteria at temperatures above freezing.

Because of the extremely advantageous aspect of avoiding the standard freezing techniques used in the prior art, the present method saves both time and money. Obviously, there is no thawing time if the bacteria are preserved at temperatures higher than freezing. Also, great cost savings come about because there is no need for expensive liquid nitrogen, which is the typical freezing agent used in the prior art. Furthermore, there is no stress from the freezing-thawing cycle, which causes the death of some of the bacteria cells as they are frozen and the death of additional cells as the thawing takes place. Additionally, since the cultures are already in suspension, there is obviated the necessity of dissolving a thawed culture in order to use it. Lastly, all of the problems accompanying frozen storage are eliminated since although the cultures preserved by the technique of the present invention may be frozen, they do not need to be. Rather, they may be stored at temperatures above freezing, preferably at a approximately 4° C., or at even higher temperatures, such as at room temperature and above. At temperatures above freezing, the bacteria will substantially retain viability, with the total possible number of days of storage generally decreasing as the temperature increases. By "substantially retain viability", it is intended to mean that during the storage time above 0° C. any change of cell count will be within a factor of 10, which is within experimental error. At temperatures up to 37° C., viability is substantially retained for at least 6 days. In a desired embodiment, the bacteria will substantially retain viability when stored at approximately 4° C. for 10 days, 20 days, or even longer time periods of 2 months or more.

DETAILED DESCRIPTION OF THE INVENTION

In the instant invention the microorganisms being stabilized in a buffered solution are bacteria that produce acid. Bacterial cells are cultured in a suitable growth media, and then harvested by standard techniques such as ultrafiltration and/or centrifugation. Before placing the culture of bacterial cells in the buffered solution, the culture concentration should be adjusted to whatever cell count is desired.

A buffered solution or suspension is prepared from water and one or more buffering agents. Cells of acid-producing bacteria are admixed in this buffered medium. Alternatively, the bacteria may be admixed in H$_2$O, followed by the addition of a buffering agent. More particularly, a carrier may be employed to add texture to the buffered solution or suspension containing the bacteria. The carrier helps keep the bacteria dispersed and thus there is less of a tendency for them to settle to the bottom of the container holding the solution.

If a carrier is employed, it must not be a specific substrate to the particular acid-producing bacteria being stabilized. By the statement that a carrier employed in the instant invention is "not a substrate", it is intended to mean the carrier is essentially not fermentable by the acid-producing bacteria, and therefore there is substantially no production of acid. Certain starches or fermentable sugars, used as carriers in the prior art, are specific substrates to acid-producing bacteria. Although acid-producing bacteria will thrive in the presence of these starches or fermentable sugars, fermentation of the substrate by the bacteria occurs as a result of which acid is produced thereby reducing the pH and causing injury to the bacterial cells.

It is especially desirable that the bacteria are preserved in a aqueous buffered solution including a carrier in the amount of 0.1-10% weight/volume, preferably 0.2-2%. The carrier is not a specific substrate for the bacteria being preserved or stabilized. Aqueous buffered solutions alone may be employed, but it is desired to include a carrier in the buffered solution to provide texture and keep the bacterial cells in suspension even though stability of the bacteria admixed in only a buffered solution may be somewhat better. As used herein, the term suspension is intended to include true suspensions and/or a physical state which would be regarded as a dispersion by some. Also, it is intended by suspension or dispersion to include those situations in which the bacteria may have settled down to the bottom of the container. The carrier, buffering agent, H$_2$O, and bacteria may be added together in any order. It is desirable that when a carrier is used it is selected from an edible material such as seaweed derivatives, like carageen and sodium alginate. Additional desirable carriers are pectin, Guar gum, Locust bean gum, xanthan gum, a polyol, a nonfermentable sugar, or an edible cellulose. These carriers are all GRAS, generally regarded as safe by the U.S. Food and Drug Administration. Preferred carriers are sodium alginates, cellulose derivatives, or polyethylene glycol (PEG).

The pH is maintained near neutral in the present invention with any of several buffering agents. The desired pH range is from approximately 6.0 to approximately 8.0. More preferably, the pH is from 6.4 to 7.6. Any buffering agent that maintains the pH around neutral may be used, as long as it does not result in the production of a substantial amount of acid, i.e., is not a specific substrate for the bacteria. The preferred buffering agents are the phosphate buffers, such as diammonium phosphate, sodium phosphate dibasic, or mixtures thereof. Magnesium phosphate, magnesium ammonium phosphate and diammonium bicarbonate are also advantageously employed as buffering agents. The aqueous buffered solution will typically contain 0.2–5% weight/volume of buffering agent.

There can also optionally be included agents such as anti-oxidants, mold inhibitors, and/or salts. Usually, such agents have little or no effect on the storage viability of the microorganisms. These agents may be added in the amount of 0.1–5% weight/volume, preferably 0.2–2% w/v of additional agent to buffered solution. Typically, a small amount of sodium benzoate is added in order to prevent mold or fungus. Also, a small amount of the organic salt, sodium citrate, may be added to help maintain osmotic pressure within the cell. If storage life is reduced by a few days, this is usually offset by the advantage of the agent, i.e., inhibition of mold.

The microorganisms preserved by the process of the present invention are the acid-producing bacteria. In general, such bacteria possess the ability to ferment simple carbohydrates, such as lactose or glucose, with lactic acid being at least one, and usually the most abundant, of the fermentation products. Among such acid-producing bacteria are *Leuconostoc cremoris, Streptococcus lactis, S. cremoris, S. diacetylactis, S. thermophilus, Lactobacillus bulgaricus, L. acidophilus, L. helveticus, L. bifidus, L. casei, L. lactis, L. plantarum, L. delbrueckii, L. thermophilus, L. fermentii,* and *Pediococcus cerevisiae.* The more preferred Lactobacilli are *Lactobacillus acidophilus, L. lactis, L. plantarum* or *Leuconostoc cremoris.* The lactic acid-producing bacteria, *L. plantarum* is employed in the following examples.

SPECIFIC EXAMPLES

The following examples of the instant invention are set forth here with the intention that they be only illustrative. It is not intended that the claims be limited thereto. The strain of *Lactobacillus plantarum* used in these examples is on deposit in the American Type Culture Collection in Rockville, Md., registered at ATCC #39542. The strain was grown and concentrated as follows:

Viable cells of *L. plantarum* were cultured in a hydrolyzed milk-based growth media which was fortified with dextrose, yeast extract, and mineral salts. NH$_4$OH was added to maintain the pH at approximately 6.5, during the culturing. Incubation was conducted for 16 to 24 hours at 37° C. Then, the culture was harvested using centrifugation with a desludger, collecting a slurry of cells. A desludger is a rotary drum with stacked plates that allow for a continuous filtration whereby mother liquor, unused growth media, and metabolic by-products are eliminated in the waste stream. Next, the slurry of cells was rinsed with physiological saline or peptone water, each of which is a washing solution having a neutral or close to neutral pH. Such washing solutions are well known in the art for use in rinsing a harvested culture of bacterial cells. They aid in removing residual material that may be present from the culture media. The filtration was continued to concentrate the freshly harvested culture of cells to whatever cell count was desired for each example below. Cell count which is used as a measure of viability was measured in CFU/ml (colony forming units per milliliter) and determined as follows: Using sterile pipets, samples of 1.0 milliliter each were transferred into tubes each of which contained 10 milliliters of cold (2° C. to 5° C.) sterile distilled peptone water (0.1%) w/v. The samples were vortexed at low speed to achieve proper mixing and several dilutions were made in the sterile 0.1% w/v peptone water. The dilutions were placed onto APT (All Purpose Tween medium from Difco) agar plates in duplicate. The plates were incubated anerobically for 48 hours at 37° C. and the CFU/ml determined by the use of a Quebec automatic colony counter. Each distinct colony on the agar plates indicates the presence of a single organism from the samples. A count of the bacterial colonies, therefore, will indicate the total number of organisms present in the sample.

EXAMPLE I

A buffer was prepared by mixing 2.8 g of $(NH_4)_2HPO_4$ in 100 cc of water. To this was added 0.7 g of sodium alginate, resulting in a prepared solution having a pH of 7.0. Next, 15 cc of a concentrated, freshly harvested culture of *Lactobacillus plantarum* with a desirable cell concentration was suspended in a small amount of this prepared solution with stirring. Additional prepared solution was added to a total volume of 50 cc, with the resultant bacterial suspension having a pH of 7.6. Cell count was determined in the manner described above and the stability data is reported below in Table I below.

TABLE I

| Days | pH | Cell Count (CFU/ml) | % Loss | Factor of 10 Loss |
|---|---|---|---|---|
| 4° C. Storage | | | | |
| 0 | 7.6 | $1.0 \times 10^{11}$ | — | — |
| 10 | 6.9 | $1.2 \times 10^{11}$ | 0 | No |
| 17 | 6.8 | $1.2 \times 10^{11}$ | 0 | No |
| 32 | 6.7 | $1.3 \times 10^{11}$ | 0 | No |
| 46 | 6.7 | $1.2 \times 10^{11}$ | 0 | No |
| 54 | 6.7 | $1.5 \times 10^{11}$ | 0 | No |
| 22° C. Storage Temperature | | | | |
| 0 | 6.7 | $9.0 \times 10^{10}$ | — | — |
| 6 | 6.6 | $4.9 \times 10^{10}$ | 46 | No |
| 15 | 6.6 | $8.9 \times 10^{9}$ | 90 | Yes |
| 21 | 6.6 | $7.6 \times 10^{8}$ | 99 | Yes |

The suspension of Example I was stored at 4° C. and 22° C.

From the data in Table I, it can be seen that viability was substantially retained during storage at 4° C. No loss of viability was observed after 54 days as the cell count was essentially constant, i.e., within a factor of 10. There was not even any percent loss. After 6 days at a temperature of 22° C. some percent loss of viability was observed, but there was no factor of 10 loss as the cell count was still at the same $10^{10}$. A loss in viability by a factor of 10, i.e., reduction of the cell count from $10^{10}$ to $10^9$, did not occur till 15 days.

EXAMPLE II 25 cc of concentrated, freshly harvested, washed *Lactobacillus plantarum* was mixed with 75 cc of a solution of 5.0% weight/volume diammonium phosphate buffer for a total volume of 100 cc and stored at different temperatures. Cell count was determined in the same manner as described above and the results are reported in Table II below.

TABLE II

The suspension of Example II was stored at 4° C., 22° C., 32° C., and 37° C.

| Days | pH | Cell Count (CFU/ml) | % Loss | Factor of 10 Loss |
|---|---|---|---|---|
| 4° C. Storage Temperature | | | | |
| 0 | 7.0 | $1.0 \times 10^{11}$ | — | — |
| 10 | 6.9 | $1.4 \times 10^{11}$ | 0 | No |
| 17 | 6.9 | $1.1 \times 10^{11}$ | 0 | No |
| 32 | 7.0 | $1.4 \times 10^{11}$ | 0 | No |
| 47 | 6.8 | $1.4 \times 10^{11}$ | 0 | No |
| 22° C. Storage Temperature | | | | |
| 0 | 7.3 | $2.3 \times 10^{10}$ | — | — |
| 4 | 7.3 | $4.5 \times 10^{10}$ | 0 | No |
| 11 | 7.2 | $3.3 \times 10^{10}$ | 0 | No |
| 18 | 7.2 | $2.1 \times 10^{10}$ | 9 | No |
| 26 | 7.2 | $1.8 \times 10^{10}$ | 12 | No |
| 32° C. Storage Temperature | | | | |
| 0 | 7.0 | $3.1 \times 10^{10}$ | — | — |
| 4 | 6.8 | $4.2 \times 10^{10}$ | 0 | No |
| 11 | 6.7 | $1.7 \times 10^{10}$ | 45 | No |
| 18 | 6.6 | $2.9 \times 10^{9}$ | 91 | Yes |
| 26 | 6.6 | $2.0 \times 10^{8}$ | 99 | Yes |
| 37° C. Storage Temperature | | | | |
| 0 | 7.2 | $2.1 \times 10^{10}$ | — | — |
| 4 | 6.9 | $3.5 \times 10^{10}$ | 0 | No |
| 11 | 6.6 | $4.0 \times 10^{9}$ | 81 | Yes |
| 18 | 6.6 | $1.0 \times 10^{8}$ | 99 | Yes |
| 26 | 6.5 | $9.0 \times 10^{7}$ | 99 | Yes |

From Table II, it can be seen that good stability can be achieved using a buffer that does not include a carrier such as PEG or sodium alginate. Viability was substantially retained as there was neither a percent loss nor a factor of 10 loss at a storage temperature of 4° C. for as many as 47 days and at a storage temperature of 22° for as many as 26 days. At 32° C., a factor of 10 loss did not occur till 18 days and at 37° C. not till 11 days.

EXAMPLE III

A buffer was prepared by mixing 5 g $(NH_4)_2HPO_4$ in 100 cc of water. To this was added 1 g PEG 3000, 1 g sodium benzoate and 0.17 g sodium citrate. Then, 25 cc of concentrated, freshly harvested, unwashed *Lactobacillus plantarum* was mixed with this solution of diammonium phosphate, polyethylene glycol 3000 (3000 is the average molecular weight), sodium benzoate and sodium citrate, and stored at different temperatures. Cell count was determined in the same manner as described above and the results of this Example are summarized in Table III below.

TABLE III

The suspension of Example III was stored at 32° C. and 37° C.

| Days | pH | Cell Count (CFU/ml) | % Loss | Factor of 10 Loss |
|---|---|---|---|---|
| 32° C. Storage Temperature | | | | |
| 0 | 7.2 | $1.1 \times 10^{10}$ | — | — |
| 6 | 6.9 | $1.1 \times 10^{10}$ | 0 | No |
| 10 | 6.5 | $1.4 \times 10^{10}$ | 0 | No |
| 19 | 6.6 | $3.6 \times 10^{9}$ | 67 | Yes |
| 37° C. Storage Temperature | | | | |
| 0 | 7.0 | $1.1 \times 10^{10}$ | — | — |

TABLE III-continued

The suspension of Example III was stored at 32° C. and 37° C.

| Days | pH | Cell Count (CFU/ml) | % Loss | Factor of 10 Loss |
|---|---|---|---|---|
| 6 | 6.8 | $6.2 \times 10^9$ | 44 | Yes |
| 10 | 6.6 | $4.8 \times 10^9$ | 56 | Yes |
| 19 | 6.5 | $5.8 \times 10^8$ | 95 | Yes |

From the data in Table III, it can be seen that at 32° C. viability was substantially retained past 10 days, with no factor of 10 loss till 19 days. At a higher temperature of 37° C., a factor of 10 loss in cell count started at 6 days.

EXAMPLE IV

The procedure of Example I was repeated, except that to prevent mold sodium benzoate was added in the amount of 1% weight/volume to the solution of sodium alginate and diammonium phosphate. Then, this prepared solution was used for suspending the *Lactobacillus plantarum*. There was substantially no change in viability as from Table I which reports data involving culture suspensions containing no mold inhibitor.

In summary, Example I illustrates the embodiment of using a buffer solution containing sodium alginate as the carrier. Table II illustrates using a buffer solution without any carrier. However, without the carrier to add texture, the bacteria tended to fall out of suspension, and thus administering this product, for instance as an oral administration to farm animals, would be difficult. Table III illustrates using a buffered solution containing PEG as the carrier together with the optional stability enhancing agents, sodium benzoate and sodium citrate.

As can be seen in Examples I and II above, no loss in viability occurs when the *Lactobacillus plantarum* is stored at 4° C., even when that storage is as long as 54 and 47 days, respectively. Furthermore, using one or more optional agents, i.e. sodium benzoate or sodium citrate has little effect on loss of viability, as can be seen from Example III.

We claim:

1. A method of preserving acid-producing bacteria which comprises suspending the acid-producing bacteria in a stablizing amount of an aqueous buffered solution containing a buffering agent and polyethylene glycol as a cell stabilizing carrier in the amount of 0.1–10% weight/volume, said solution being free of a specific fermentable substrate for the bacteria, thereby providing a suspension of bacteria having enhanced viability.

2. The method of claim 1, wherein the resultant suspension of bacteria has a pH between approximately 6.0 and approximately 8.0.

3. The method of claim 2, wherein said bacteria are lactic acid-producing bacteria derived from a freshly harvested culture.

4. The method of claim 3, wherein said freshly harvested culture is rinsed with a washing solution prior to admixing the bacteria in the aqueous buffered solution.

5. The method of claim 1, wherein the buffering agent in said buffered solution is diammonium phosphate, sodium phosphate dibasic diammonium bicarbonate or a mixture thereof.

6. The method of claim 5, further including an additional agent selected from the group consisting of antioxidants, mold inhibitors and salts.

7. The method of claim 6, wherein the mold inhibitor is 0.1–5% weight/volume sodium benzoate and the salt is 0.1–5% weight/volume sodium citrate based on the buffered solution.

8. A composition comprising a suspension of viable acid-producing bacteria and an aqueous buffered solution containing a buffering agent and polyethylene glycol as a cell stabilizing carrier in the amount of 0.1–10% weight/volume, said solution being free of a specific fermentable substrate for the bacteria.

9. The composition of claim 8, wherein said suspension has a pH from approximately 6.0 to approximately 8.0 wherein said pH is achieved with a buffering agent selected from the group consisting of diammonium phosphate, sodium phosphate dibasic, diammonium bicarbonate and mixtures thereof, and said bacteria are selected from the group consisting of *Leuconostoc cremoris, Streptococcus lactis, S. cremoris, S. diacetylactis, S. thermophilus, Lactobacillus bulgaricus, L. acidophilus, L. helveticus, L. bifidus, L. casei, L. lactis, L. plantarum, L. delbrueckii, L. thermophilus, L. fermentii* and *Pediococcus cerevisiae*.

* * * * *